US00RE44943E

(19) United States
(12) Reissued Patent
O'Brien

(10) Patent Number: US RE44,943 E
(45) Date of Reissued Patent: Jun. 10, 2014

(54) FLUID PROPERTIES EVALUATION

(75) Inventor: Vincent T. O'Brien, Unley (AU)

(73) Assignee: Commonwealth Scientific and Industrial Research Organisation, Australian Capital Territory (AU)

(21) Appl. No.: 13/591,593

(22) Filed: Aug. 22, 2012

Related U.S. Patent Documents

Reissue of:

(64) Patent No.: 7,054,766
Issued: May 30, 2006
Appl. No.: 10/475,297
PCT Filed: Apr. 18, 2002
PCT No.: PCT/AU02/00484
§ 371 (c)(1),
(2), (4) Date: Apr. 28, 2004
PCT Pub. No.: WO02/086462
PCT Pub. Date: Oct. 31, 2002

(30) Foreign Application Priority Data

Apr. 23, 2001 (AU) ..... PR4582

(51) Int. Cl.

| | |
|---|---|
| ***G06F 17/00*** | (2006.01) |
| ***G01L 7/00*** | (2006.01) |
| ***G01N 11/00*** | (2006.01) |
| ***G01N 11/04*** | (2006.01) |
| ***G01N 11/16*** | (2006.01) |
| ***G01N 35/08*** | (2006.01) |

(52) U.S. Cl.
CPC ..... *G01N 11/04* (2013.01); *G01N 11/165* (2013.01); *G01N 35/085* (2013.01)
USPC ..... 702/50; 73/54.24; 137/10; 422/68.1

(58) Field of Classification Search
CPC ... G01N 11/04; G01N 11/165; G01N 35/085; G01N 2035/00227; G01N 2035/0097
USPC ..... 702/33, 45, 50, 51, 100, 114; 73/54.09, 73/54.24, 54.28; 137/10; 435/293.1; 700/281, 282; 422/68.1
See application file for complete search history.

(56) References Cited

U.S. PATENT DOCUMENTS

| | | | | |
|---|---|---|---|---|
| 4,334,424 | A * | 6/1982 | Kepes | 73/54.28 |
| 5,750,884 | A * | 5/1998 | Field | 73/54.24 |
| 6,023,962 | A * | 2/2000 | Wang et al. | 73/54.09 |
| 6,357,281 | B1 * | 3/2002 | Wilhelm | 73/54.24 |
| 6,534,010 | B2 * | 3/2003 | Sentmanat | 422/68.1 |
| 6,539,968 | B1 * | 4/2003 | White et al. | 137/10 |
| 6,562,616 | B1 * | 5/2003 | Toner et al. | 435/293.1 |

FOREIGN PATENT DOCUMENTS

| | | | |
|---|---|---|---|
| AU | 31075/77 | A | 6/1979 |
| EP | 1 213 575 | A1 | 6/2002 |
| FR | 2 772 129 | A1 | 6/1999 |
| GB | 2306670 | A | 5/1997 |
| WO | WO 95/12822 | A | 5/1995 |
| WO | WO 97/210990 | A | 6/1997 |

* cited by examiner

*Primary Examiner* — John H Le
(74) *Attorney, Agent, or Firm* — Sughrue Mion, PLLC

(57) ABSTRACT

Fluid flow properties often dictate the performance of processing operations. The present invention relates to a system for evaluating properties of a fluid flowing in a pipe. A test cell (20) which includes two parallel surfaces (5, 6) which are positioned in the flow. One of the surfaces is moveable relative to the other, to a position in close proximity to the other, to create a stagnant flow region between the surfaces. The system further includes a test input device (10) to apply input motion to one of the surfaces, and a test output device (13) to measure output motions from the cell in response to input motions. Furthermore, the system includes a processing device (9) to calculate rheological parameters of the fluid from signals produced from the test input and test output device. There is also a process for evaluating properties of a flowing fluid.

27 Claims, 1 Drawing Sheet

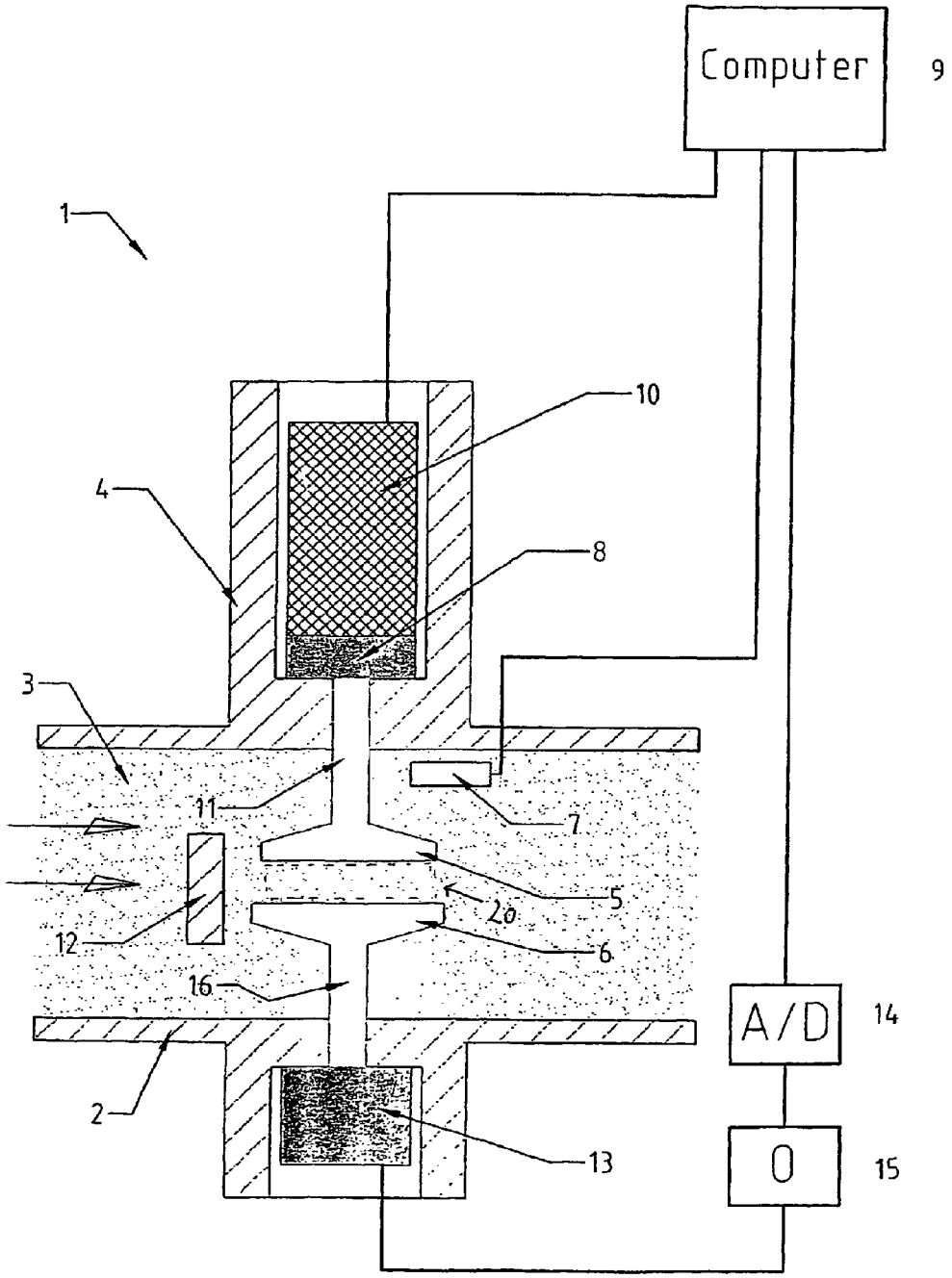
Computer
9
1
10
4
8
3
11
7
5
2a
12
6
16
A/D
14
2
13
O
15

FLUID PROPERTIES EVALUATION

Matter enclosed in heavy brackets [ ] appears in the original patent but forms no part of this reissue specification; matter printed in italics indicates the additions made by reissue.

This application is a 371 of PCT/AU02/00484, filed Apr. 18, 2002; the disclosure of which is incorporated herein by reference.

TECHNICAL FIELD

This invention concerns a system for evaluating properties of a flowing fluid. In another aspect, it concerns a test cell to evaluate the properties of a flowing fluid. In a further aspect it concerns a method for evaluating properties of a flowing fluid.

BACKGROUND ART

Rheology concerns the deformation and flow of matter. Materials can resist deformation in a solid-like manner or in a viscous-like manner. Solid-like materials store energy under deformation, upon removal of the stress, the material returns to its undeformed state. Viscous-like materials dissipate stress during deformation. Materials with combined solid-like and viscous-like properties are said to be viscoelastic.

Most materials such as foodstuffs, paints, gels and polymer melts are viscoelastic in nature. Their viscoelasticity is often essential to performance criterion and consequently oscillatory strain techniques have been developed for measuring these properties. The solid-like or viscous-like nature is quantified from the stress response to an oscillatory strain. In ideal solid-like materials, the stress response will be in phase with the oscillatory strain, ie the largest deformation will coincide with the largest stress. Viscous-like materials do not store energy and the stress developed depends on the rate of deformation. Consequently, the stress response will be out of phase with the oscillatory strain. In viscoelastic materials, the stress will be between 0° and 90° out of phase with the deformation, displaying viscous-like and solid-like properties. Storage modulus is defined as a measure of the solid-like or in-phase stress response. The loss modulus measures the fluid-like response.

Rheological, particuarly viscosity, measurements are important for process control. Flow properties often dictate the performance of processing operations. Highly viscous products may be undesirable due to expensive pumping costs, however low viscosity products may be prone to settling problems. Flow properties may be critical to performance in the desired end use. For example, the surface roughness of painted films during and after application is controlled through tailoring very specific flow resistance in paint products. Furthermore, flow properties are dictated by the inherent material microstructures. Consequently, rheological measurements that gauge material conversion rates and addition levels during processing may predict many performance criterion after processing.

SUMMARY OF THE INVENTION

In a first aspect the invention is a system for evaluating properties of a flowing fluid comprising:

a section of pipe through which the fluid flows;

a test cell positioned in the pipe and presenting two parallel surfaces in line with the flow, one of which is moveable relative to the other, to a position in close proximity to the other, to create a stagnant flow region between the surfaces, a test input means to apply input motions to one of the surfaces;

a test output means to measure output motions from the cell in response to the input motions; and processing means to calculate rheological parameters of the fluid from signals produced from the test input and test output means.

The system is able to measure the rheological properties of the fluid while it is flowing in the pipe. The advantages of fluid capture and testing in a process stream are that the fluid remains unpolluted, requiring low maintenance of the system, that measurements of complex viscosity and viscoelastic properties can be made quickly and on demand, and that quantified measurements can be available for effective process control.

In another aspect, the invention is a test cell to evaluate properties of a flowing fluid, comprising: p a housing having an aperture for fluid to flow through and two parallel surfaces in the aperture in line with the flow, one of which is moveable relative to the other;

a test input means to apply input motions to one of the surfaces; and a test output means to measure output motions from the cell in response to the input motions.

A temperature sensor may be positioned in the fluid flow to measure the temperature of the fluid. In high fluid flows, a shield may be appropriately positioned upstream of the test cell to assist in the creation of a stagnant flow.

The test input means may be an actuator. The test input means may include a motion sensor to determine the waveform of the input motion. The test input means may apply mechanical or electrical vibrations to the surface and may use rotational, harmonic or piston methods. The input motion may be a single wave such as a sine wave, square wave, triangular wave, sawtooth wave, or the like, or alternative, may be a complex signal having for instance a waveform formed from the superposition of two or more single sine waves, square waves, triangular waves, or sawtooth waves, where each wave is of a different frequency.

An analogue to digital converter and a power amplifier may be provided to drive the test signal input means.

A shield may be provided near the surfaces to assist in trapping fluid between the cell surfaces.

The processing means may include a computer, an analogue to digital converter and a power amplifier. The processing means may further include computer software to assemble input signal waveforms; store output signal data; compensate and adjust for drift occurring between the cell surfaces; and implement sampling regimes for the system to perform.

In another aspect, the invention is a process for evaluating properties of a flowing fluid, comprising the following steps:

positioning two parallel surfaces in line with the flow, moving one of the surfaces relative to the other, to a position in close proximity to the other, to create a stagnant flow region between the surfaces, applying input motions to one of the surfaces;

measuring output motions from the cell in response to the input motions; and calculating rheological parameters of the fluid from signals produced from the test input and test output means.

BRIEF DESCRIPTION OF DRAWINGS

An example of the invention will now be described with reference to the accompanying drawing, FIG. 1, which is a diagram of a rheometer.

BEST MODE FOR CARRYING OUT THE INVENTION

Referring to FIG. 1, the rheometer 1 is connected directly to a pipe 2 through which flows a process stream 3. A housing 4 of the rheometer 1 is fixed to the walls of the pipe 2. Two parallel smooth plates 5 and 6 extend from the housing into the pipe in line with the flow to form a test cell 20. The bottom plate 6 may be of complex design to reduce or eliminate edge effects and compensate for the non-compressibility of many fluids which may be measured in this immersed environment.

The rheometer 1 has an actuator stage 10 inside the housing 4 and a shaft 11, to connect it to the upper moveable plate 5. The shaft is provided with a thermal barrier so as to limit the heat flow out of the chamber. The cell also has a temperature sensor 7 such as a thermocouple or thermistor mounted in the stream. A piezoelectric AC transducer 13 is attached to the bottom plate 6 in the cell. Seals are provided to prevent ingress of the measured fluid around the shafts 11 and 16.

The actuator 10 is provided with a motion sensor 8 to determine the actual waveform applied to the plate 5. A processing means such as a computer 9 is connected to the rheometer with an attaching analogue to digital converter 14 and preamplifier 15 to control and process results from the rheometer.

If the flow rate of the fluid is too high, preventing a stagnant region forming between the two plates, a shield 12 may be used to assist in the trapping of fluid between the plates.

The actuator 10 is capable of providing motion to the cell surfaces in a direction perpendicular to the centroid axis of the cell, or alternatively it may be in a direction orthogonal to the axis. The actuator is generally axisymmetric with the test cell 20 and situated directly above it to generate oscillatory displacements with a resolution of greater than a tenth of a micron. The motion provided by the actuator may be a single sine wave, square wave, triangular wave, sawtooth wave, or the like, or a complex signal having for instance any waveform formed from the superposition of two or more single sine waves, square waves, triangular waves, or sawtooth waves, of different frequencies.

In Use

Sample collection is achieved by using the actuator stage 10 to drive the upper plate 5 towards the lower plate 6 and squeezing them together until a stagnant flow region forms within the test cell 20. In circumstances where the flow rate of the process stream 3 is too fast, insertion of an appropriately placed shield, or baffle, 12 may be required to assist in creating the stagnant flow region. When the stagnant flow region is formed, there may still be some small flow between the two plates (5, 6), but this drift may be corrected and compensated for in the rheological calculations by software.

When fluid capture is achieved, measuring commences by oscillating the top plate 5 with the desired waveform, x(t). Forces generated by the oscillation are determined, G(t) from the piezoelectric transducer 13. Alternatively, the force measuring means may take the form of measuring the voltage necessary to drive the actuator 10. Oscillation is applied in a random or pseudo random reciprocating movement to one of the plates in a direction normal to the other plate by the actuator. Movements include squeeze flow, extensional flow, rotational, torsional or orthogonal to be used as the basis of the rheological measurement. For these measurements, the control of the sample fluid is achieved by controlling the velocity of sample fluid relative to the time taken for the fluid to pass through the cell. The signal from the motion sensor is used in a feedback loop to increase the voltage when the motion amplitude falls below that required by the waveform definition.

There are no limitations in respect to the signal processing, allowing any torsional movement to be processed to calculate the complex modulus of the fluid. Waveforms are assembled by the computer software and stored as a repeating pattern of numbers representing amplitude. The rate at which these numbers are read determines the frequency range. From the oscillation of the top plate, the complex transfer function may then be calculated as:

$$TF(\omega) = \frac{\Im[G(t)]}{\Im[x(t)]}$$

automatically, where the operator $\Im$ indicates Fourier transforms. The viscosity and viscoelastic parameters are then calculated using:

$$G^*(\omega) = \frac{h^3}{3\pi a^4} TF(\omega)$$

This operation can be repeated and averaged several times by the software to improve resolution of rheological data. After the software calculates the rheological parameters, the sample is ejected by first squeezing the plates together driving the tested sample out of the test cell 20. The plates are then separated allowing flow in the process stream to scrub the plate surfaces and prevent residue build up or fouling of the test cell 20.

The rheometer is designed to run continuously as part of a production process with little or no operator intervention. The rheometer relies on continuous cycles of sample collection, measurement and sample ejection. This continuous sampling provides savings in time and allows the collation of rheological data to be more accurately calculated through multiple sampling. The sampling regime may be automatically controlled by computer software, and administered at various time intervals.

In an alternative embodiment, the rheometer can also be connected to a bypass stream for on-line operation. This may be suitable when there are very large amounts of flowing fluid or when there is difficulty in installing the system to a process stream such as limited space. Fluid capture and measurement are performed similar to the preferred embodiment Furthermore, an electromagnetic motor may replace the alternator 10 to drive the upper plate 5 towards the lower plate 6.

In another alternative embodiment, the housing 4 of the rheometer 1 may extend into the flow in pipe 2. In such an embodiment, a diaphragm may cover the bottom surface of the top plate to prevent flow escaping from the pipe. In a still alternate embodiment, the plates (5, 6) may be concentric cylinders.

Alternative techniques available for measuring rheological properties are rotation of the upper plate or harmonic vibration of the upper plate. Rotational methods apply large rotational strains to samples thereby generating equilibrium stress. Harmonic types resonate the upper plate. Fluid viscosity is calculated from either the change in harmonic frequency, amplitude or current required to maintain constant amplitude.

In additon to the flat plates described parallel lenses or concentric cylinders may be used.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A system for evaluating properties of a flowing fluid comprising: a section of pipe through which the fluid flows; a test cell positioned in the pipe and presenting two parallel surfaces in line with the flow, one of which is moveable relative to the other, to a position in close proximity to the other, to create a stagnant flow region between the surfaces[,];

a test input means to apply input motions to one of the surfaces;

a test output means to measure output motions from the cell in response to the input motions; and processing means to calculate rheological parameters of the fluid from signals produced from the test input and test output means*; wherein the input motions are substantially perpendicular to the surfaces*.

2. A system according to claim 1, further comprising a temperature sensor positioned in the fluid flow.

3. A system according to claim 1, further comprising a shield positioned upstream of the test cell to assist in the creation of a stagnant flow.

4. A system according to claim 1, wherein the test input means is an actuator.

5. A system according to claim 1, wherein the test input means includes a motion sensor to determine the waveform of the input motion.

6. A system according to claim 1, wherein the input motion comprises a complex waveform.

7. A system according to claim 1, wherein the test output means is a piezoelectric transducer.

8. A system according to claim 1, wherein the processing means comprises:

a computer;

an analogue to digital converter; and a power amplifier.

9. A system according to claim 8, wherein the processing means further comprises computer software to perform at least one of the following: assemble input signal waveforms;

store output signal data;

compensate and adjust for drift occurring between the cell surfaces; and implement sampling regimes for the system to perform.

10. A test cell to evaluate properties of a flowing fluid, comprising:

a housing having an aperture for fluid to flow through and two parallel surfaces in the aperture in line with the flow, one of which is moveable relative to the other to a position in close proximity to the other to create a stagnant flow between the surfaces;

a test input means to apply input motions to one of the surfaces; and a test output means to measure output motions related to calculations of rheological parameters from the cell in response to the input motions*; wherein the input motions are substantially perpendicular to the surfaces*.

11. A test cell according to claim 10, further comprising a temperature sensor positioned in the fluid flow.

12. A test cell according to claim 10, further comprising a shield positioned upstream of the test cell to assist in the creation of a stagnant flow.

13. A test cell according to claim 10, wherein the test input means is an actuator.

14. A test cell according to claim 10, wherein the test input means includes a motion sensor to determine the waveform of the input motion.

15. A test cell according to claim 10, wherein the input motion comprises a complex waveform.

16. A test cell according to claim 10, wherein the test output means is a piezoelectric transducer.

17. A test cell according to claim 10, wherein the processing means comprises:

a computer;

an analogue to digital converter; and a power amplifier.

18. A test cell according to claim 17, wherein the processing means further comprises computer software to perform at least one of the following:

assemble input signal waveforms;

store output signal data;

compensate and adjust for drift occurring between the cell surfaces; and implement sampling regimes for the system to perform.

19. A process for evaluating properties of a flowing fluid, comprising the following steps:

positioning two parallel surfaces in line with the flow to define a test cell therebetween;

moving one of the surfaces relative to the other, to a position in close proximity to the other, to create a stagnant flow region between the surfaces; applying input motions to one of the surfaces;

measuring output motions from the cell in response to the input motions; and calculating rheological parameters of the fluid from signals produced from test input and test output means*; wherein the input motions are substantially perpendicular to the surfaces*.

20. A process according to claim 19, further comprising a temperature sensor positioned in the fluid flow.

21. A process according to claim 19, further comprising a shield positioned upstream of the test cell to assist in the creation of a stagnant flow.

22. A process according to claim 19, wherein the test input means is an actuator.

23. A process according to claim 19, wherein the test input means includes a motion sensor to determine the waveform of the input motion.

24. A process according to claim 19, wherein the input motion comprises a complex waveform.

25. A process according to claim 19, wherein the test output means is a piezoelectric transducer.

26. A process according to claim 19, wherein the processing means comprises:

a computer;

an analogue to digital converter; and a power amplifier.

27. A process according to claim 26, wherein the processing means further comprises computer software to perform at least one of the following: assemble input signal waveforms;

store output signal data;

compensate and adjust for drift occurring between the cell surfaces; and implement sampling regimes for the system to perform.

* * * * *